(12) United States Patent
Hansen et al.

(10) Patent No.: US 7,468,101 B2
(45) Date of Patent: Dec. 23, 2008

(54) UV VARNISH GLOSS PERFORMANCE USING NOVEL PIGMENT AND PROCESS FOR MAKING SAME

(75) Inventors: Colin Wayne Hansen, Alburtis, PA (US); Larry Joseph Zeiner, Nazareth, PA (US); Neil V. Pagotto, Bethlehem, PA (US)

(73) Assignee: Specialty Minerals (Michigan) Inc., Bingham Farms, MI (US)

( * ) Notice: Subject to any disclaimer, the term of this patent is extended or adjusted under 35 U.S.C. 154(b) by 0 days.

(21) Appl. No.: 11/505,605

(22) Filed: Aug. 17, 2006

(65) Prior Publication Data

US 2008/0041275 A1 Feb. 21, 2008

(51) Int. Cl.
*C09C 1/02* (2006.01)
*C01F 11/18* (2006.01)

(52) U.S. Cl. .................. 106/464; 162/181.2; 423/430; 424/49; 524/425

(58) Field of Classification Search ............... 106/464; 162/181.2; 423/430; 424/49; 524/425
See application file for complete search history.

(56) References Cited

U.S. PATENT DOCUMENTS

| | | | | |
|---|---|---|---|---|
| 4,133,894 A | * | 1/1979 | Shibazaki et al. | 423/432 |
| 4,242,318 A | | 12/1980 | Brahm et al. | |
| 4,714,603 A | | 12/1987 | Vanderheiden | |
| 5,085,800 A | * | 2/1992 | Minayoshi et al. | 516/33 |
| 5,292,365 A | | 3/1994 | Delfosse | |
| 5,833,747 A | | 11/1998 | Bleakley et al. | |
| 5,861,209 A | * | 1/1999 | Haskins et al. | 428/330 |
| 6,123,855 A | * | 9/2000 | Hansen et al. | 210/723 |
| 6,143,065 A | * | 11/2000 | Freeman et al. | 106/464 |
| 6,156,286 A | * | 12/2000 | Fortier et al. | 423/432 |
| 6,402,824 B1 | | 6/2002 | Freeman et al. | |
| 6,475,459 B1 | * | 11/2002 | Virtanen | 423/432 |
| 6,500,400 B1 | * | 12/2002 | Kinnen et al. | 423/432 |
| 6,602,484 B1 | * | 8/2003 | Virtanen | 423/430 |
| 6,620,856 B1 | | 9/2003 | Mortimer et al. | |
| RE38,301 E | | 11/2003 | Bleakley et al. | |
| 6,790,424 B2 | * | 9/2004 | Jasra et al. | 423/274 |
| 7,135,066 B1 | * | 11/2006 | Nafus et al. | 106/447 |
| 2002/0172636 A1 | * | 11/2002 | Nover et al. | 423/432 |
| 2004/0256067 A1 | * | 12/2004 | Leskela et al. | 162/142 |

FOREIGN PATENT DOCUMENTS

| | | | | |
|---|---|---|---|---|
| CA | 2237960 A | * | 12/1998 | |
| JP | 46-14821 A | * | 4/1971 | |
| JP | 63-230520 A | * | 9/1988 | |
| JP | 3-894 A | * | 1/1991 | |
| JP | 2004-189518 | | 7/2004 | |
| WO | WO2004/016566 A1 | * | 2/2004 | |
| WO | WO2006/011872 A1 | * | 2/2006 | |

OTHER PUBLICATIONS

Derwent-Acc-No. 2001-352052, abstract of RD441091A (Jan. 2001).*
Derwent-Acc-No. 2005-159248, abstract of Korean Patent Specification No. KR 500731B (Jul. 2005).*
International Search Report dated Dec. 12, 2007, issued in counterpart international patent application No. PCT/US07/18328, forwarded in communication dated Jan. 24, 2008.
Written Opinion dated Dec. 12, 2007, issued in counterpart international patent application No. PCT/US07/18328, forwarded in communication dated Jan. 24, 2008.

* cited by examiner

*Primary Examiner*—Anthony J Green
(74) *Attorney, Agent, or Firm*—Leon Nigohosian, Jr.

(57) ABSTRACT

A high solids precipitated calcium carbonate (PCC) suspension and method for producing the suspension are provided, with the PCC having a PCC particle size distribution $d_{90}$ value of about 0.7 microns or less, a PCC particle size distribution $d_{50}$ value of about 0.4 microns or less, a PCC particle size distribution $d_{90}/d_{50}$ ratio of from about 1.2 to about 2.2 and a PCC specific surface area of about 10.0 meters squared per gram or greater.

11 Claims, 3 Drawing Sheets

UV VARNISH GLOSS PERFORMANCE USING NOVEL PIGMENT AND PROCESS FOR MAKING SAME

The invention relates to high solids calcium carbonate suspensions and particularly to high solids precipitated calcium carbonate (PCC) suspensions and their method of production.

Ultraviolet (UV) radiation-cured coatings are used as overprint varnishes, hereinafter referred to as "UV varnishes", to impart a glossy appearance and excellent abrasion resistance to coated paper or coated paperboard, hereinafter referred to as a "substrate". In a typical UV varnish application process, a printed image is applied to a substrate by any of a number of known printing techniques including, but not limited to flexographic printing, offset printing, rotogravure printing and the like. A UV varnish is then applied to the printed and unprinted areas, after which the UV varnish coated area is exposed to a UV radiation source to cross-link or cure the UV varnish onto the substrate. The resulting cross-linked or cured UV varnish coating imparts a high gloss, abrasion-resistant protective finish to the substrate.

As a coating pigment, precipitated calcium carbonate (PCC) provides excellent optical properties to the resulting coated paper or coated paperboard. The narrow particle size distribution of the PCC particles results in a coating that provides excellent light scattering and brightness. The narrow particle size distribution of PCC particles also creates a structure within the coating layer that contains pores or voids. The presence of these pores or voids further enhances the light scattering and brightness properties of the PCC coating. However, when a UV varnish, which is typically a relatively low viscosity liquid, is applied to this porous or open structure coating layer created by the PCC, the UV varnish penetrates into the coating layer prior to being cross-linked or cured by the UV irradiation source. This phenomenon is more pronounced on the unprinted areas of the substrate. The result is that the UV varnish does not provide the same level of gloss or abrasion-resistance that it would have if it did not penetrate into the coating layer.

The foregoing illustrates limitations known to exist in the use of conventional PCC coating pigments in applications where UV varnishes are used. Thus, it is apparent that it would be advantageous to provide an alternative directed to overcoming one or more of the limitations set forth above. Accordingly, high solids PCC suspensions, their method of production and use as a paper coating pigment on paper products to which a UV varnish is applied are provided, including the features more fully disclosed hereinafter.

SUMMARY

In some embodiments, a high solids PCC suspension is provided. The high solids PCC suspension has a PCC particle size distribution $d_{90}$ value of about 0.7 microns or less. The high solids PCC suspension has a PCC particle size distribution $d_{50}$ value of about 0.4 microns or less. The high solids PCC suspension has a PCC particle size distribution $d_{90}/d_{50}$ ratio of from about 1.2 to about 2.2. The high solids PCC suspension has a PCC specific surface area of about 10.0 meters$^2$ per gram or greater.

In some embodiments, a process for producing a high solids PCC suspension comprises: providing a first suspension of PCC, concentrating the first suspension of PCC to obtain a second suspension of PCC having a solids content of about 72 percent by weight or greater, and flash milling the second suspension of PCC to produce a final suspension of PCC.

In some embodiments, a high solids PCC suspension is used as a paper coating pigment.

In some embodiments, a high solids PCC suspension is used as a paper filler.

In some embodiments, a high solids PCC suspension is used as an additive in paints and polymers such as, but not limited to, plastics, sealants and the like.

DETAILED DESCRIPTION

Some embodiments of the invention provide high solids PCC suspensions, their method of production and/or use as a paper coating pigment.

Figure 1:
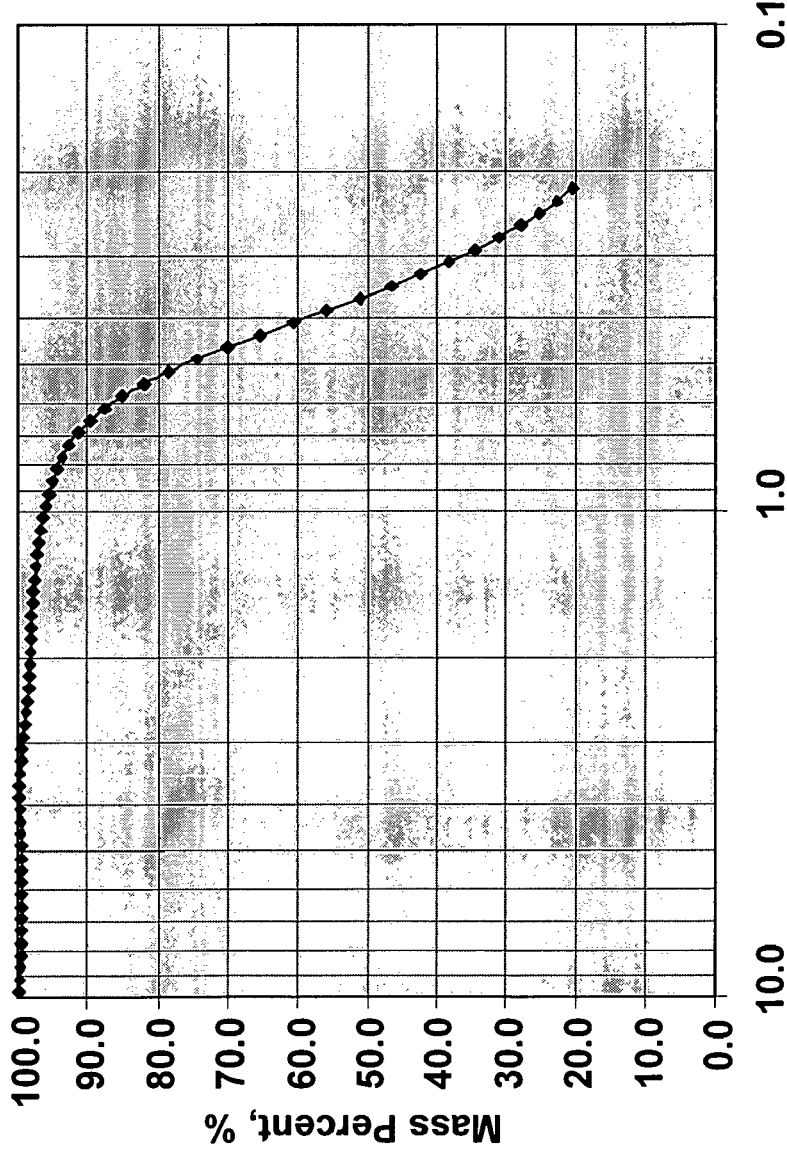
FIG. 1 is a particle size distribution (PSD) curve of a PCC produced in some embodiments.

In some embodiments, the high solids PCC suspension generally comprises acicular particles of calcium carbonate having a predominately aragonitic morphology. An exemplary particle size distribution (PSD) curve of the high solids PCC suspension is shown in FIG. 1 and generally comprises PCC particles having a particle size distribution $d_{90}$ value of about 0.66 microns, a particle size distribution $d_{50}$ value of about 0.36 microns and a particle size distribution $d_{90}/d_{50}$ ratio of about 1.8.

In other embodiments, the high solids PCC suspension generally comprises PCC particles having a particle size distribution $d_{90}$ value of about 0.7 microns or less, a particle size distribution $d_{50}$ value of about 0.4 microns or less, a particle size distribution $d_{90}/d_{50}$ ratio of from about 1.2 to about 2.2 and a specific surface area of about 10.0 meters$^2$ per gram or greater.

In further embodiments, the high solids PCC suspension generally comprises PCC particles having a particle size distribution $d_{90}$ value of about 0.5 microns or less. In some embodiments, the high solids PCC suspension generally comprises PCC particles having a particle size distribution $d_{90}$ value of from about 0.5 microns to about 0.7 microns.

In some embodiments, the high solids PCC suspension generally comprises PCC particles having a particle size distribution $d_{50}$ value of about 0.35 microns or less. In some embodiments, the high solids PCC suspension generally comprises PCC particles having a particle size distribution $d_{50}$ value of from about 0.32 microns to about 0.36 microns.

In some embodiments, the high solids PCC suspension generally comprises PCC particles having a specific surface area of from about 11.0 meters$^2$ per gram to about 14.0 meters$^2$ per gram.

In some embodiments, the as-produced high solids PCC suspension generally comprises a PCC solids content of about 72 percent by weight or greater. In other embodiments, the high solids PCC suspension may be adjusted to generally comprise a PCC solids content of less than about 72 percent by weight to suit commercial or manufacturing needs. In some embodiments, the as-produced high solids PCC suspension generally comprises a PCC solids content of from about 73 percent by weight to about 75 percent by weight. In other embodiments, the as-produced PCC solids content may be greater than 75 percent by weight.

As used herein, the term "particle size distribution $d_{90}$ value" is defined as the numerical value, usually expressed in microns, at which 90 percent of the mass or volume fraction of particles have particle sizes which are less than or equal to that value. As used herein, the term "particle size distribution $d_{50}$ value" is defined as the numerical value, usually expressed in microns, at which 50 percent of the mass or volume fraction of particles have particle sizes which are less than or equal to that value.

As used herein, the term "predominately aragonitic morphology" applies to PCC particles having an aragonite content of from about 75 percent to about 100 percent, as determined by x-ray diffraction (XRD) analysis. In some embodiments, the high solids PCC suspension generally comprises PCC particles having an aragonite content of from about 85 percent to about 98 percent, as determined by XRD analysis.

As used herein, the term "specific surface area" is defined as the Brunauer-Emmett-Teller (BET) specific surface area of the PCC particles contained in a dry powder sample of PCC, as measured on a Micromeritics FlowSorb II single point surface area instrument manufactured by the Micromeritics Instrument Corporation, Georgia.

Figure 2:
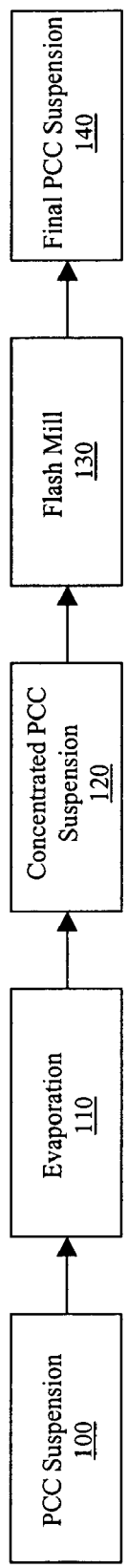
FIG. 2 is an schematic flow chart of a process for producing a high solids PCC suspension in some embodiments.

An exemplary process is shown in FIG. 2 and generally comprises providing a dispersed aqueous suspension of PCC 100 having a solids content of about 73% by weight or less (e.g., from about 68 percent by weight to about 71 percent by weight), concentrating the PCC suspension 110 (e.g., by thermal evaporation), optionally under reduced pressure to obtain a concentrated PCC suspension 120 having a PCC solids content of from about 73 percent by weight to about 74 percent by weight and flash milling 130 the concentrated PCC suspension to produce a final PCC suspension 140.

A dispersed aqueous suspension of PCC having a solids content of from about 70 percent by weight to about 71 percent by weight is commercially available from Specialty Minerals, Inc., Bethlehem Pa. and is sold under the tradename OPACARB® A40 Precipitated Calcium Carbonate (PCC). Other PCC suspensions having a solids content lower than 70 percent may be used as a starting material, with a commensurate concentration step (e.g., thermal evaporation performed for a longer time, at a greater temperature and/or at a lower pressure).

The step of concentrating the PCC suspension by thermal evaporation, optionally under reduced pressure to obtain a concentrated PCC suspension having a PCC solids content of about 72 percent by weight or higher can be achieved using process equipment known in the art including, but not limited to heat exchangers, film evaporators, multiple effect evaporators, vacuum flash columns and the like. In some embodiments, a vacuum flash column as described in U.S. Pat. No. 6,454,907, which is incorporated by reference herein in its entirety, may be used to increase the solids of a PCC suspension to a final solids concentration of about 72 percent solids by weight or higher. Alternatively, other thermal evaporation methods, whether previously known or developed in the future, may be used.

As used herein, the term "flash milling" is defined as a milling process that is carried out at an energy input of less than about 50 kilowatt hours per dry ton of material being milled. The step of flash milling the concentrated PCC suspension to produce a final PCC suspension having good rheological properties can be achieved using process equipment known in the art including, but not limited to media mills, sand mills and the like, or future developed process equipment. In one embodiment, flash milling may be carried out by introducing the concentrated PCC suspension into a media mill containing grinding media such as glass, steel, sand, ceramic media including, but not limited to, aluminum oxide, zirconium oxide, zirconium silicate and the like or other media known in the art, of a size from about 0.2 mm to about 5.0 mm.

In alternative embodiments, in which the concentrating step provides a PCC solids concentration less than about 73%, the milling step may use an elevated milling energy input (between about 50 kilowatt hours per dry ton of material being milled and about 100 kilowatt hours per dry ton). The amount of energy required in the milling step depends on the solids concentration at the completion of the concentrating step.

In other embodiments, a non-aragonitic PCC feed material may be used. Use of non-aragonitic PCC feed material may require an elevated milling energy input (substantially greater than about 50 kilowatt hours per dry ton of material being milled) and may result in a Specific Surface Area (SSA) that is substantially greater than 14 meter$^2$/gram. After final processing, one may simply dilute to the suspension to lower the solids—the final UV gloss property will be maintained.

The high solids PCC suspension described herein is particularly useful as a coating pigment for paper and paperboard products. Other uses for the high solids PCC suspension described herein may include, but are not limited to, use as a filler material for paper and paperboard, or as an additive for paints and polymers such as, but not limited to, plastics, sealants and the like.

EXAMPLES

The following non-limiting examples are merely illustrative embodiments of the present teachings and are not to be construed as limiting the invention.

In the examples described below, particle size distribution values were determined based on sedimentation techniques using a Micromeritics Sedigraph model 5100 instrument manufactured by the Micromeritics Instrument Corporation, Georgia.

Example 1

A high solids dispersed slurry of predominantly aragonitic precipitated calcium carbonate (OPACARB® A40 Precipitated Calcium Carbonate (PCC), available from Specialty Minerals, Inc., Bethlehem, Pa.) was introduced as a 70 percent solids slurry (hereinafter described as "PCC feed material") into a vacuum flash column (VFC) during which the slurry was recirculated through a pump having an in-line rotor-stator unit (IKA® model no. HED 150, IKA® Works, Inc., Wilmington, N.C.). The VFC was operated at about 0.1 bar pressure with slurry temperature of about 120 degrees Fahrenheit. The PCC slurry was recirculated through the VFC until a slurry solids content of about 74 percent solids by weight was achieved.

Upon discharge from the VFC, the resultant 74 percent solids PCC slurry was flash milled through an 8P CB Mill (Chicago Boiler Co., Gurnee, Ill.) at 25 kilowatt hours per dry PCC ton energy input. The CB mill was operated using a 100% by volume charge of zirconium silicate media of from about 0.6 millimeters to about 0.8 millimeters diameter. Particle size characteristics of the initial PCC feed material and the final high solids product are summarized in Table 1. The final product can be used as a 74 percent solids slurry or can be adjusted to a lower weight percent solids, depending on commercial and application requirements.

TABLE 1

High Solids PCC Feed Material and Final High Solids PCC Product

| | PCC Feed Material | Final High Solids PCC Product |
|---|---|---|
| % Solids | 70.1 | 74.2 |
| PSD $d_{90}$, microns | 0.78 | 0.65 |
| PSD $d_{50}$, microns | 0.39 | 0.35 |
| PSD $d_{90}/d_{50}$ ratio | 2.0 | 1.9 |
| Specific Surface Area (SSA), $m^2/g$ | 11.6 | 11.9 |

Example 2

A bleached paperboard having a basis weight of 210 grams per square meter was blade-coated on the Cylindrical Laboratory Coater 6000 (SimuTech International, Inc., Hoodsport, Wash.) at a speed of 1500 feet per minute. The paperboard was pre-coated with 10 grams per square meter of a coating grade ground calcium carbonate (HYDROCARB® 60 Ground Calcium Carbonate, Omya Inc., Proctor, Vt.).

Some of the pre-coated paperboard was top-coated with 10 grams per square meter of a coating formulation containing 70 parts of a commercially-available dispersed slurry of coating grade PCC (OPACARB® A40 PCC) and 30 parts of a premium glossing grade coating clay at a coating color solids of 65 percent by weight.

Some of the pre-coated paperboard was top-coated with 10 grams per square meter of a coating formulation containing 70 parts of a coating formulation containing 70 parts of the high solids PCC suspension described herein and 30 parts of a premium glossing grade coating clay at a coating color solids of 65 percent by weight.

Figure 3:
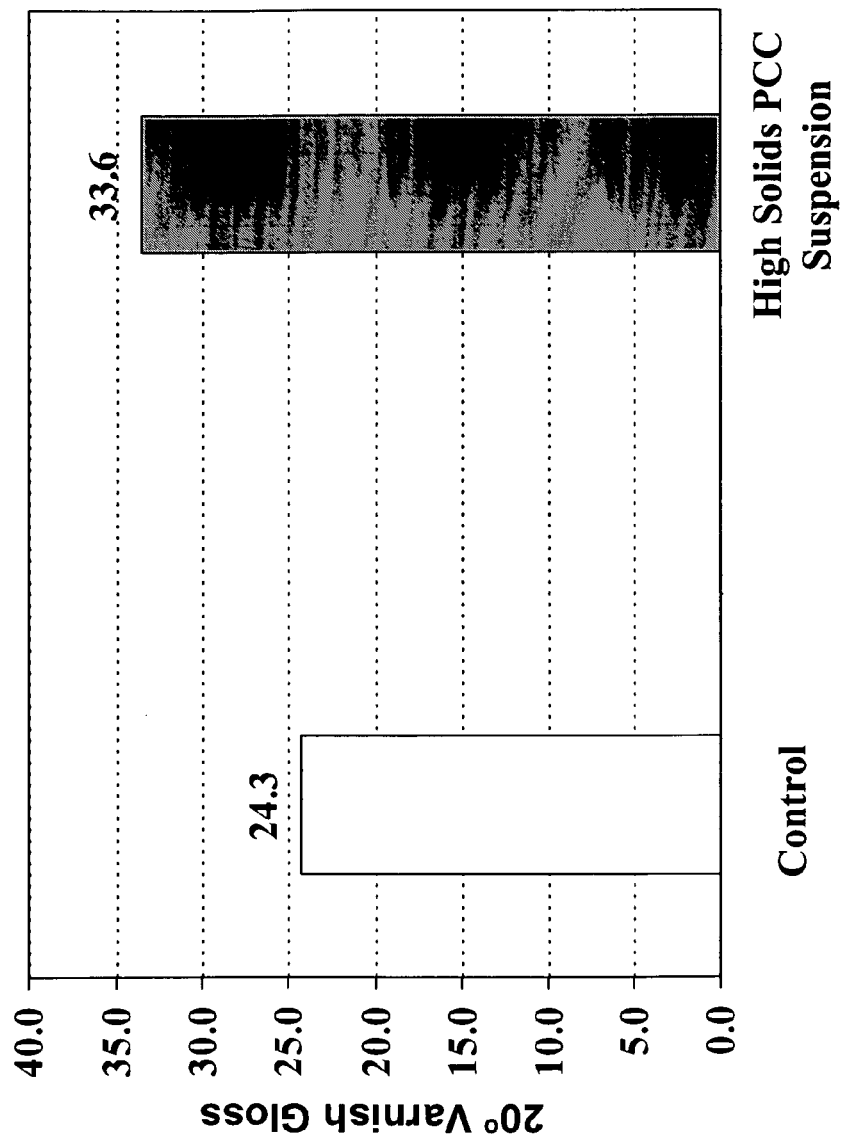
FIG. 3 is a bar graph of the 20° varnish gloss for a paper coated with a commercially available PCC compared to a PCC according to an embodiment of the invention.

All coated paperboard samples were calendered using a Beloit Wheeler Laboratory Calender (Beloit Corporation, Otsego, Mich.), operated using one nip, ambient temperature and a load of 300 pounds per square inch. Varnish (SUN-CURE® SF 1738-NS, Sun Chemical Corp., Parsippany, N.J.) was applied to the coated paperboard samples with the Prüfbau Multipurpose Printability Tester (Prüfbau GmbH, Munich, Germany) and cured with a mini conveyorized UV curing unit (American Ultraviolet Co., Lebanon, Ind.) at 300 watts per inch. The Gardco Statistical Novogloss unit (Paul N. Gardner Co., Inc., Pompano Beach, Fla.) was used for all 20° gloss measurements in accordance with the manufacturer's instructions. The 20° varnish gloss values for paper coated with a commercially available dispersed slurry of the commercially available coating grade PCC control and the high solids PCC suspension described herein are shown in FIG. 3.

The results show the improved UV varnish gloss properties obtained with the high solids PCC suspension compared to a commercially available PCC coating pigment control.

While embodiments and applications have been shown and described, it will be apparent to those skilled in the art that modifications are possible without departing from the inventive concepts herein described. It is understood, therefore, that the invention is capable of modification and therefore is not to be limited to the precise details set forth. Rather, various modifications may be made in the details within the scope and range of equivalents of the claims without departing from the spirit of the invention.

What is claimed is:

1. A precipitated calcium carbonate (PCC) suspension comprising PCC particles and having:
    a PCC particle size distribution $d_{90}$ value of about 0.7 microns or less;
    a PCC particle size distribution $d_{50}$ value of about 0.4 microns or less;
    a PCC particle size distribution $d_{90}/d_{50}$ ratio of from about 1.2 to about 2.2; and
    a PCC specific surface area of about 10.0 meters squared per gram or greater.

2. The precipitated calcium carbonate (PCC) suspension of claim 1, wherein the PCC particles have a particle size distribution $d_{90}$ value of about 0.5 microns or less.

3. The precipitated calcium carbonate (PCC) suspension of claim 1, wherein the PCC particles have a particle size distribution $d_{50}$ value of about 0.35 microns or less.

4. The precipitated calcium carbonate (PCC) suspension of claim 1, wherein the PCC particles have an aragonite content of from about 75 percent to about 100 percent.

5. The precipitated calcium carbonate (PCC) suspension of claim 1, wherein the PCC particles have an aragonite content of from about 85 percent to about 98 percent.

6. The precipitated calcium carbonate (PCC) suspension of claim 1, wherein the suspension has a PCC solids content of about 72 percent by weight or greater.

7. The precipitated calcium carbonate (PCC) suspension of claim 1, wherein the suspension has a PCC solids content of less than about 72 percent by weight.

8. A paper or paperboard coated with the precipitated calcium carbonate of claim 1.

9. A paper or paperboard filled with the precipitated calcium carbonate of claim 1.

10. A toothpaste containing the precipitated calcium carbonate of claim 1.

11. A polymer containing the precipitated calcium carbonate of claim 1.

* * * * *